(12) United States Patent
Tai et al.

(10) Patent No.: US 7,692,141 B2
(45) Date of Patent: Apr. 6, 2010

(54) POLYMER BASED ELECTROSPRAY NOZZLE FOR MASS SPECTROMETRY

(75) Inventors: Yu-Chong Tai, Pasadena, CA (US); Xuan-Qi Wang, San Diego, CA (US); Amish Desai, Altadena, CA (US); Terry D. Lee, San Diego, CA (US); Lawrence Licklider, Jamaica Plain, MA (US)

(73) Assignees: California Institute of Technology, Pasadena, CA (US); City of Hope, Duarte, CA (US)

( * ) Notice: Subject to any disclaimer, the term of this patent is extended or adjusted under 35 U.S.C. 154(b) by 231 days.

(21) Appl. No.: 11/942,647

(22) Filed: Nov. 19, 2007

(65) Prior Publication Data

US 2008/0185515 A1 Aug. 7, 2008

Related U.S. Application Data

(60) Division of application No. 11/472,392, filed on Jun. 22, 2006, now Pat. No. 7,297,943, which is a continuation of application No. 09/442,843, filed on Nov. 18, 1999, now abandoned.

(60) Provisional application No. 60/109,264, filed on Nov. 19, 1998, provisional application No. 60/114,900, filed on Jan. 5, 1999.

(51) Int. Cl.
- H01J 49/04 (2006.01)
- H01J 49/26 (2006.01)
- B01D 59/44 (2006.01)

(52) U.S. Cl. .................... 250/288; 250/281; 250/282; 250/423 R; 250/424; 210/748

(58) Field of Classification Search ............... 250/288, 250/281, 282, 423 R, 424; 210/748
See application file for complete search history.

(56) References Cited

U.S. PATENT DOCUMENTS

| 7,105,812 | B2 * | 9/2006 | Zhao et al. | 250/288 |
| 7,297,943 | B2 * | 11/2007 | Tai et al. | 250/288 |
| 7,541,578 | B2 * | 6/2009 | Weng | 250/288 |
| 2006/0193748 | A1 * | 8/2006 | Tai et al. | 422/70 |

* cited by examiner

*Primary Examiner*—Nikita Wells
(74) *Attorney, Agent, or Firm*—Foley & Lardner LLP

(57) ABSTRACT

A MEMS device with an overhanging 'polymer' capillary provides vital and significant improvements in interfacing a MEMS electrospray nozzle to an MS inlet or other macroscopic instrumentation. The fabrication methodology associated therewith is easily expanded to include built-in micro particle filters and centimeter long serpentine micro channels provided on-chip and fabricated using a low temperature process.

19 Claims, 3 Drawing Sheets

POLYMER BASED ELECTROSPRAY NOZZLE FOR MASS SPECTROMETRY

CROSS REFERENCE TO RELATED APPLICATIONS

This application claims the benefit of U.S. Provisional Application No. 60/114,900, filed on Jan. 5, 1999, and U.S. Provisional Application No. 60/109,264, filed on Nov. 19, 1998.

STATEMENT AS TO FEDERALLY SPONSORED RESEARCH

The U.S. Government may have certain rights in this invention pursuant to a Grant No. 2 R01 RR06217-06 awarded by the National Institute of Health.

FIELD OF THE INVENTION

This disclosure relates to chip-based chemical analysis systems such as electrospray mass spectroscopy (MS). More specifically, this disclosure relates to fabrication of a micron-sized micro-electromechanical systems ("MEMS") electrospray nozzle.

BACKGROUND

Over the past decade, there has been increasing interest in the development of miniaturized chemical analysis systems using micro-electromechanical (MEMS) technology. Until more recently, the prior art in MEMS technology has included UV absorbance and electro-chemi-luminescence for on-chip detection. These optical methods are not viable for detection of many biomolecules. A viable commercial product should be able to process/analyze a wide range of samples.

Mass spectrometers ("MS") are one type of widely used macroscopic instrument for the analysis of biomolecular structures such as proteins, carbohydrates, lipids and polynucleotides. MS is widely used due to its ability to analyze large proteins and peptides. MS also has high sensitivity, e.g., as high as $10^{-12}$ moles.

Much experimentation has focused on an on-chip interface that has the advantage of directly coupling a MEMS electrospray nozzle to an MS inlet.

SUMMARY

The present disclosure describes a MEMS device with an overhanging 'polymer' capillary that allows interfacing a MEMS electrospray nozzle to an MS inlet or other macroscopic instrumentation. The fabrication methodology associated therewith is easily expanded to include built-in micro particle filters and centimeter long serpentine micro channels provided on-chip and fabricated using a low temperature process.

In an embodiment, the core structured material is parylene polymer, aluminum and photoresist are used as sacrificial layers, and bromine trifluoride ($BrF_3$) gas phase etching is employed for final microcapillary releasing.

BRIEF DESCRIPTION OF THE DRAWINGS

These and other aspects will be described with reference to the drawings, in which.

DESCRIPTION OF THE PREFERRED EMBODIMENTS

Electrospray ionization (ESI) can be used with MEMS chemical systems to generate ions for MS analysis.

ESI is an atmospheric pressure ionization technique in which gaseous ionized molecules are produced in a fine spray from a liquid droplet in the presence of a strong electric field between a capillary tip and an MS inlet. The released ionized molecules are then directed into the MS inlet by the applied field. The applied electric field changes the shape of the fluid droplet from a spherical shape to a cone called the Taylor cone. The base of this cone is dependent on the geometry and the wetted area (wall thickness) of the capillary. Hence, reduction of these parameters reduces the size of the Taylor cone, thus reducing dead-volume.

ESI can form a simple and direct way to interface a MEMS device to a mass spectrometer. The MEMS device needs an electrospray nozzle from which fluid can be injected toward the mass spectrometer inlet.

The capability to fabricate micron-sized tips with micromachining is advantageous in many ways: 1) the shape and finish of the tip can be reproducible from chip to chip, 2) complex MEMS filter structures can be constructed inside the micromachined liquid channel in order to filter out debris, and 3) mass production is available due to batch processing.

Figure 1:
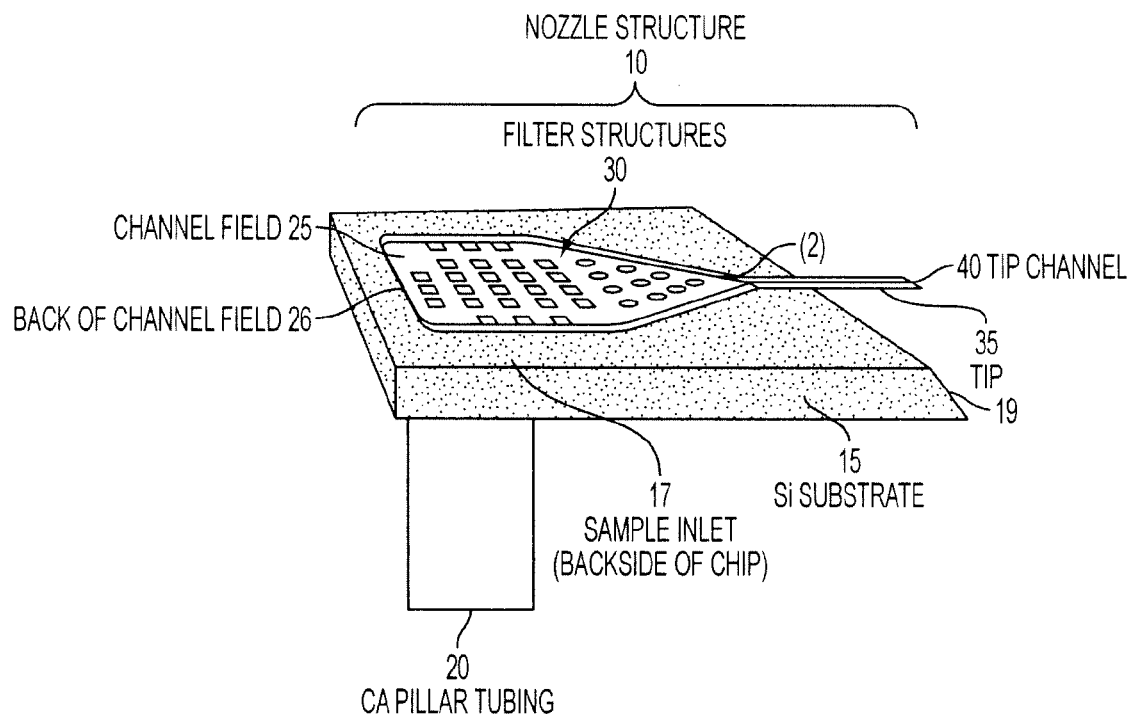
FIG. 1 shows a three dimensional view of a silica-based micromachined electrospray nozzle.

A silica-based micromachined nozzle construction is shown in FIG. 1. The silica-based nozzle structure 10 is shown constituted by a support silicon substrate 15. The support silicon substrate 15 is formed to have a sample inlet window 17. The sample inlet window 17 is positioned on the underside of the silicon substrate 15 in contact with the nozzle structure 10, represented by dashed lines. A capillary tubing 20 is attached to the sample inlet window 17 to supply liquid sample into the nozzle structure 10.

The liquid sample is intended for flow into the channel field 25 of the nozzle structure 10. In the illustrated nozzle structure, the channel field 25 is a micro-channel formed with multiple filter structures 30.

The silica-based nozzle structure 10 is formed by a "sandwich" fabrication sequence. The sequence involves depositing two silicon nitride ($Si_xN_y$) layers on the silicon substrate 15 during the manufacturing process to form outer portions of a sandwich. An interior/sacrificial layer of phosphosiligate glass (PSG) material is deposited between the sandwiching $Si_xN_y$ nitride layers and this interior layer selectively etched to form the illustrated filter structures which function as filters and space inhibitors in the interior of the channel field 25. The channel field 25 and the tip channel 35 occupy the volume where the PSG layer was located before the PSG layer is etched away.

The nozzle structure 10 is ultimately finally etched to form the nozzle structure with an overhanging electrospray capillary. The tip orifice of the nozzle structure is micron-sized. This resultant MEMS device with its overhanging micro-channel was found to reduce the wetted surface area at the ESI tip. Reduction of this orifice diameter and tip surface area correspondingly reduce the size of the fluid cone during electrospray, thus reducing the internal volume that the liquid occupies from the inlet of the device to the actual point of analysis. This internal volume is called the dead volume. In addition to reducing dead volume, the nozzle has integrated particle filter structures that function to reduce MEMS ESI tip clogging.

An outward sloping sidewall 19 combined with the short length (1) of the silicon nitride nozzle tip 35 limits the tip-to-inlet distance as well as interferes with the electric field profile at the channel tip end. Furthermore, it is well known that fabrication of mm-long silicon nitride overhanging structures poses significant challenges. $Si_xN_y$ capillaries longer than a few hundred microns can curve due to film stress gradients (typically 200 MPa for LPCVD $Si_xN_y$). To achieve channels longer than a few hundred microns long, etching holes on $Si_xN_y$ channels are necessary. Such etching holes can be sealed after sacrificial layer etching. Etching holes not only complicate the process, but the resulting stress concentration around such etching holes could cause released microchannels to easily crack. Another drawback is that the fragile silicon nitride capillaries shatter with the slightest contact with the MS inlet during chemical analysis.

Many of the above-mentioned drawbacks of $Si_xN_y$ ESI tips are found to be eliminated with an overhanging "polymer"-based nozzle structure 50 described below in connection with FIGS. 2-4. The polymer material utilized is Parylene-C ("Parylene"). Parylene is a bio-compatible polymer material used to make MEMS microchannels and microvalves. The properties of Parylene produce advantages when forming an improved nozzle structure. In contrast to the silica-based nozzle structure 10, polymer material is ideal for fabrication of high aspect ratio overhanging structures due to its low tensile stress (<100 Mpa).

Because Parylene allows for deposition at room temperature, a photoresist is used in place of the sacrificial material used in the fabrication of silica-based nozzle structures. Unlike PSG etching, a photoresist sacrificial etching (with acetone) does not require etching holes along the channel. Thus, structures that are orders of magnitude longer can be easily fabricated. The Young's modulus of Parylene (~3 GPa) is only about one hundredth of $Si_xN_y$. In terms of robustness, the fabricated Parylene microcapillaries are far superior. While $Si_xN_y$ capillaries can shatter easily with the slightest contact with other objects, Parylene capillaries, even when up to 600 times longer, flex and return to their original shape.

Parylene ESI tips possess improved plasticity. Despite a longer overhanging tip structure than $Si_xN_y$ ESI tips, Parylene ESI tips were found to even be able to survive table-top falls and mishandling without having the tips break. In short, the robustness of the parylene nozzles coupled with the simple to manufacture process makes polymer-based technology very much more commercially viable.

Figure 2:
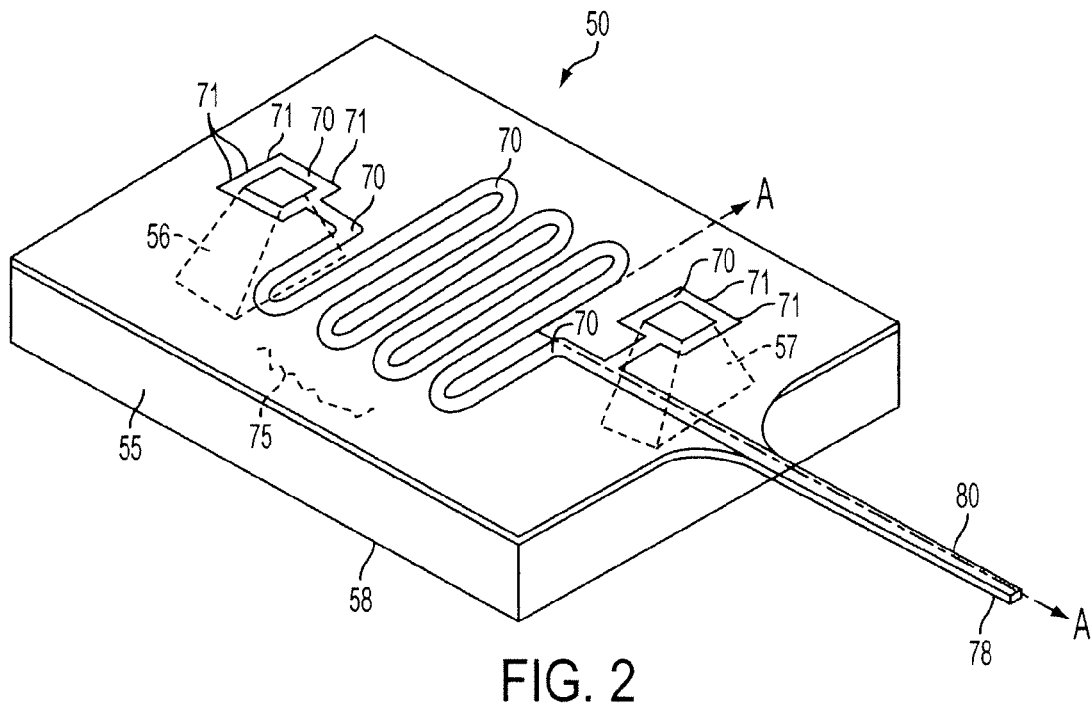
FIG. 2 shows a three dimensional view of a polymer-based micromachined electrospray nozzle constructed in accordance with the present invention.

An illustrative embodiment of a polymer-based nozzle structure 50 is shown in FIG. 2. The polymer-based nozzle structure is a micromachined electrospray-type nozzle formed on a support substrate 55, preferably a silicon substrate. The support substrate 100 is formed with first and second inlet windows 56 and 57 (shown in dashed lines). Inlet windows 56, 57 extend vertically through the silicon substrate 55 to make contact, at an underside thereof, with a capillary tubing through which is to be supplied liquid sample(s) during chemical analysis.

The liquid sample flows into a filtered channel field 70 of the nozzle structure 50. In the illustrative nozzle structure, the filtered channel field 70 is a micro-channel comprised of circumferentially integrated filter elements 71 formed about each of first and second inlet windows 56 and 57. Filtered channel field 70 further comprises serpentine channels 75 disposed downstream from the back of the channel field 25 closest to first inlet window 56. Both filter elements 71 and serpentine channels 75 function to separately trap debris and other particles in the liquid sample.

Liquid sample introduced to nozzle structure 50 through first inlet window 56 travels through associated filter elements 71 downstream, through serpentine channels 75, and ultimately out through a substantially rectangularly-shaped orifice at tip channel 78 extending axially through microcapillary tip 80.

Liquid sample introduced to nozzle structure 50 through second inlet window 57 bypasses filtration through the serpentine channels 75.

It should be appreciated that while serpentine channels and filter elements have been shown as a manner to provide filtration, other orientations are possible. For example, the nozzle structure 50 may be fabricated with only serpentine channels, or only with filter elements, and such may be of variable dimensions and sizes. An important consideration in designing the positioning of filtration means is selecting appropriate spacing and dimensioning so as to achieve sufficient filtration. Clogging between the nozzle-structure Parylene layers by particulates in the liquid sample also must be considered.

Use of more than one sample inlet window 56, 57 facilitates mixing or adding other liquids to the sample before ionization.

FIGS. 3A to 3F will now be used to explain the fabrication steps associated with the formation of a polymer-based nozzle structure. FIGS. 3A to 3F only show a limited cross-section of the nozzle structure 50 of FIG. 2 taken along zigzag path A-A'.

The nozzle structure 50 is generally similar in fabrication to the "sandwich" layering of the silica-based nozzle structure 10 shown in FIG. 1. However, instead of $Si_xN_y$ upper and lower layers, two Parylene polymer layers are used to form layers that will eventually become the floor and roof of the nozzle structure 50.

The polymer-based "sandwich" is constituted by a 5 μm thick photoresist 110 enclosed by two Parylene layers 101, 102, each 3 μm thick on a 500 μm thick silicon substrate 55. The overhanging capillary nozzle structure 50 is created by gas phase etching of the Si support substrate 55 underneath.

Nozzle structure 50 could be formed on a 1 cm×0.7 cm die. Serpentine channels may be either 5 or 10 cm long, for example, and selected based on desired separation. Of course, all dimensions are only exemplary and may be varied based on liquid sample properties and flow requirements.

Figure 3A:
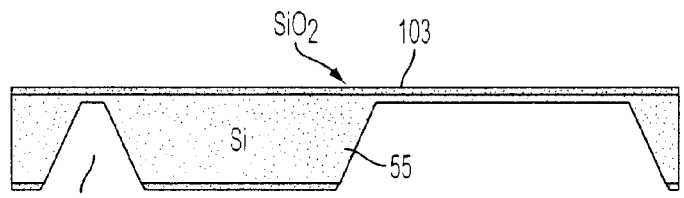
FIG. 3 shows the fabrication sequence of the nozzle in FIG. 2.
Figure 3B:
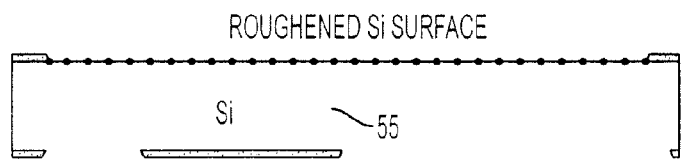
Figure 3C:
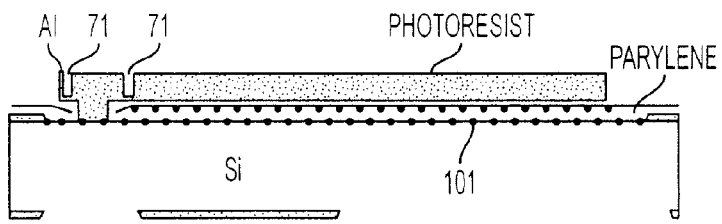
Figure 4A:
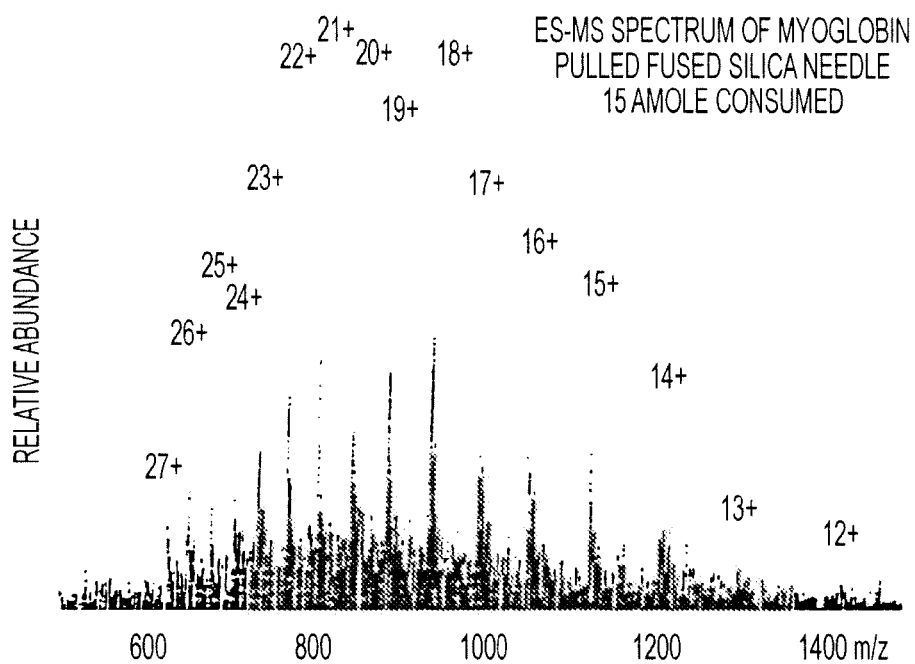
FIG. 4 shows a mass spectrum analysis of myoglobin using a polymer-based nozzle structure vs. a silica-based nozzles structure.
Figure 4B:
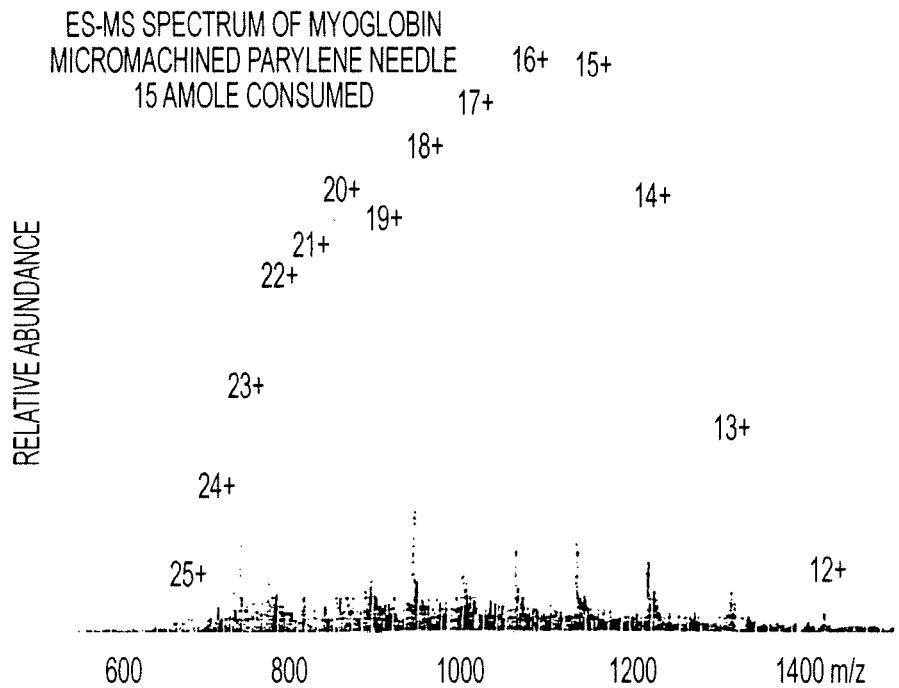

During fabrication, appropriate windows 57 are opened in a silicon wafer preferably coated on both sides with 1.5 μm silicon dioxide (FIG. 3A). Next, backside cavities are etched by potassium hydroxide (KOH) to leave a 10 μm silicon membrane left with a $SiO_2$ mask layer 103. The $SiO_2$ layer on wafer top side is patterned and etched with BHF. $BrF_3$ gas phase etching follows, to roughen the silicon surface for adhesion enhancement (FIG. 3B). Next, a 3 μm thick layer 101 of Parylene is deposited on the wafer front side only. After patterning the Parylene with oxygen plasma, a 5000 Å thick Al layer is evaporated and patterned to form filter elements 71 (FIG. 3C).

Figure 3D:
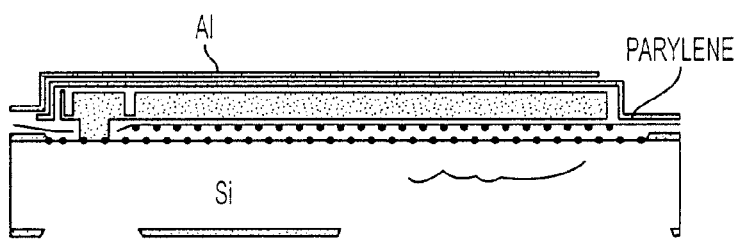
Figure 3E:
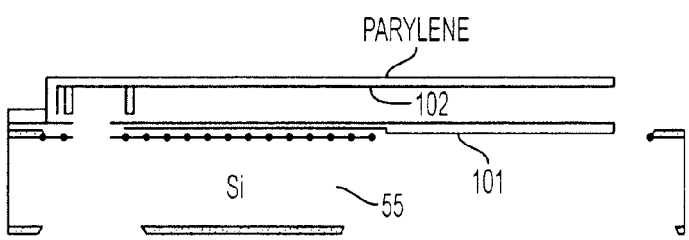

A photoresist layer of 5 μm thickness is then spun and patterned. The wafer is then hard baked at 120° C. for 10 minutes to evaporate the solvent in the photoresist. Baking helps prevent buckle and burst if heat is applied later on. A 3 μm thick Parylene layer 102 is then deposited on the front side. A 0.1 μm thick Al layer evaporated and patterned as a masking layer thereover follows this. Afterwards, oxygen plasma etching is performed and the microcapillary tip 80 is given form (FIG. 3D). Next, the wafer is diced, and the thin silicon membrane is etched away with BrF$_3$ to open up the backside inlet window 56 and release the overhanging polymer tip 80 (FIG. 3E).

Figure 3F:
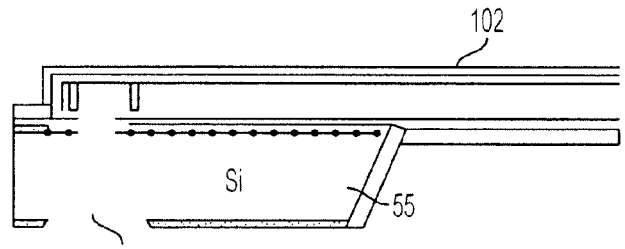

The photoresist layer is then dissolved away with acetone to establish the channel field 25 through which liquid sample flows downstream and out to tip 80. The MEMS nozzle structure 50 is eventually rinsed and immersed in alcohol and deionized water for several hours (FIG. 3F).

To minimize tip clogging, particle filters can also be incorporated in several other designs by employing a double sacrificial material method. Using sub-micron channel heights in the filter areas, and larger channel heights for the remaining microchannel length forms filter elements 71. To achieve this type of bi-level sacrificial structure, careful control of both thicknesses is essential. In a preferred embodiment, a sub-micron Al layer is used for the filter region and a thicker photoresist for the rest of the structure. The flexibility of polymer material selected must also be taken into account when designing structures that are subject to mechanical pressure. For example, fluidic pressure can cause deformation in the sub-micron filter area and nullify its effectiveness as a sub-micron filter. To address this deformation problem, polymer anchor structures are fabricated in this region to hold the top and bottom of the channel together.

The gas phase silicon etchant BrF$_3$ is used to release the microcapillaries. This etching method serves two purposes in this process: 1) to partially roughen the silicon surface for increased adhesion to the Parylene, and 2) to release the microcapillaries from the silicon substrate 55 in the last fabrication step.

Compared to other silicon etching methods, plasma etching offers less silicon undercutting and tends to damage the Parylene film on the structure. Even though potassium hydroxide (KOH) or tetramethyl ammonium hydroxide (TMAH) do not attack Parylene at low temperature, they do attack the Parylene-silicon interface significantly and cause Parylene to peel off from the substrate. In contrast, the gas phase silicon isotropic etchant, BrF$_3$, can etch silicon spontaneously at room temperature and maintain the integrity of a Parylene-silicon interface.

The ability to fabricate precise micrometer-sized tip geometries expands the uses of micro-electrospray phenomena. In addition to experimentally derived empirical data, mathematical models also facilitate prediction calculations. For instance, the following mathematical model models a circular cone with a specific cone tip angle, where $r_e$ represents the radius of the emission region at the tip of the Taylor cone, $\gamma$ the surface tension of the liquid, $\rho$ the density of the liquid, $U_a$ the applied voltage, $U_t$ the voltage at which the cone is formed, $\upsilon$ the cone angle, and dV/dt the flow rate. The equation below predicts that $r_e$, the emission radius can be reduced with a reduction in flow rate. However, in the illustrative nozzle structure 50, the orifice through the tip 80 is rectangular and initial measurements of the cone angle show significant deviation from that of a circular capillary Taylor cone (~49°).

$$r_e = \left( \frac{\rho}{4\pi^2 \gamma \left[ \left( \frac{U_a}{u_t} \right)^2 - 1 \right] \tan\left( \frac{\pi}{2} - \upsilon \right)} \right)^{1/3} \cdot \left( \frac{dV}{dt} \right)^{2/3}$$

The improved polymer-base nozzle structure makes possible coupling a MEMS device to an MS interface. The nozzle structure represents vital and significant improvements in MEMS process technology and MS functionality with respect to the silicon-nitride ESI nozzles reported before. The tests validate the tremendous advantages and viability of Parylene polymer technology particularly when combined with gas phase etching to form mm-long rugged overhanging capillary structures. The integration of micro-particle filters sandwiched between polymer layers has made the nozzle a more convenient tool for MS. In the context of a MEMS application for chemical analysis, the invention renders MEMS ESI more cost-efficient and practical.

Employed as a MEMS device, the nozzle structure now has the possibility to be integrated with other chip-based chemical analysis systems, thus increasing the potential of high sensitivity chemical detection with MEMS systems.

Although only a few embodiments have been described in detail above, those having ordinary skill in the art will certainly understand that many modifications are possible in the preferred embodiment without departing from the teachings thereof.

All such modifications are intended to be encompassed within the following claims.

What is claimed is:

1. A method of fabricating a polymer-based micromachined electrospray nozzle structure, comprising:
   obtaining a support substrate;
   first forming a first polymer layer on said support substrate which will form a floor of said nozzle structure;
   first patterning said first layer to form a first inlet window;
   second forming an interior layer over said first layer;
   second patterning a portion of said interior layer to form a filtered channel field, said filtered channel field forming a path through which fluid can flow;
   third forming a second polymer layer, said second layer forming a roof of said polymer-based nozzle structure; and
   first etching said support substrate to expose a nozzle tip and releasing said first inlet window.

2. A method as in claim 1, wherein said support substrate is silicon.

3. A method as in claim 1, wherein said first and second polymer layers are Parylene layers.

4. A method as in claim 1, wherein said interior layer is a photoresist layer.

5. A method as in claim 1, wherein said filtered channel field comprises filter elements disposed around the first inlet window.

6. A method as in claim 5, wherein said filtered channel field further comprises serpentine channels disposed downstream, relative to the flow of fluid, from the first inlet window.

7. A method as in claim 6, wherein said step of first patterning said first layer to form a first inlet window, also forms a second inlet window.

8. A method as in claim 1, wherein said filtered channel field comprises serpentine channels disposed downstream, relative to the flow of fluid, from the first inlet window.

9. A method as in claim 1, wherein said step of first patterning said first layer to form a first inlet window, also forms a second inlet window.

10. A method as in claim 1, wherein prior to said first forming a first polymer layer on said support substrate, gas phase etching a surface of the support substrate.

11. A method as in claim 10, wherein said gas phase etching is done with bromine trifluoride (BF$_3$).

12. A method as in claim 1, wherein said polymer-based nozzle structure is a MEMS device adapted for coupling to an inlet of a mass spectrometer using electrospray ionization (ESI).

13. A micromachined polymer-based apparatus, comprising:

a support substrate;

a nozzle structure formed on said support substrate and defined by at least a first and second polymer layers and an interior layer, wherein said first and second polymer layers are Parylene layers; and a first inlet window formed on said nozzle structure and adapted for receiving, from a capillary tube, a sample into said nozzle structure via said first inlet window.

14. An apparatus as in claim 13, wherein said interior layer is a photoresist layer.

15. An apparatus as in claim 13, wherein said interior layer defines a filtered channel field comprising filter elements disposed around the first inlet window.

16. An apparatus as in claim 15, wherein said filtered channel field further comprises serpentine channels disposed downstream, relative to the flow of fluid, from the first inlet window.

17. An apparatus as in claim 16, further comprising a second inlet window formed on said nozzle structure and adapted for receiving, from a different capillary tube, a sample into said nozzle structure via said second inlet window.

18. An apparatus as in claim 13, wherein said interior layer defines a filtered channel field comprising serpentine channels disposed downstream, relative to the flow of fluid, from the first inlet window.

19. An apparatus as in claim 13, wherein said nozzle structure is a MEMS device adapted for coupling to an inlet of a mass spectrometer using electrospray ionization (ESI).

* * * * *